US00PP20232P3

(12) United States Plant Patent
Colfer

(10) Patent No.: US PP20,232 P3
(45) Date of Patent: Aug. 25, 2009

(54) ARTICHOKE PLANT NAMED 'PS-MSG0417'

(50) Latin Name: *Cynara scolymus L.*
Varietal Denomination: PS-MSG0417

(75) Inventor: William J. Colfer, Aptos, CA (US)

(73) Assignees: Plant Sciences, Inc., Watsonville, CA (US); Ocean Mist Farms, Castroville, CA (US)

( * ) Notice: Subject to any disclaimer, the term of this patent is extended or adjusted under 35 U.S.C. 154(b) by 420 days.

(21) Appl. No.: 11/416,318

(22) Filed: May 3, 2006

(65) Prior Publication Data

US 2007/0214526 P1 Sep. 13, 2007

Related U.S. Application Data

(60) Provisional application No. 60/780,862, filed on Mar. 10, 2006.

(51) Int. Cl.
*A01H 5/00* (2006.01)

(52) U.S. Cl. ..... Plt./258
(58) Field of Classification Search ..... Plt./258
See application file for complete search history.

*Primary Examiner*—Susan B McCormick Ewoldt
(74) *Attorney, Agent, or Firm*—Foley & Lardner LLP

(57) ABSTRACT

A new and distinct cultivar of artichoke plant named 'PS-MSG0417', characterized by its numerous bud numbers, fleshiness of bracts, fleshiness of hearts, high fecundity rate and uniformity of head shapes.

2 Drawing Sheets

Latin name of the genus and species of the plant claimed: *Cynara scolymus L.*
Variety denomination: 'PS-MSG0417'.

BACKGROUND OF THE INVENTION

The present invention comprises a new and distinct cultivar of artichoke plant, botanically known as *Cynara scolymus L.,* and herein referred to by the cultivar name 'PS-MSG0417'.

*Cynara scolymus L.,* commonly known as Globe artichoke, is a thistle-like perennial herb and is a member of the family Asteraceae, also known as the Compositae family. Globe artichokes comprise: leaves, which are pinnately lobed; but primarily spiney; oval capitula composed of overlapping layers of large volucral bracts; and receptacles, which are enlarged and fleshy. Globe artichoke plants may be propagated by division or vegetative means, and are essentially grown for the production of the immature flower heads, which are considered as vegetable delicacies. Fresh artichokes may be baked, steamed, or boiled, after which the fleshy receptacle, inner and outer bracts, and parts of the floral stem may be eaten.

The new *Cynara* cultivar is a product of a planned breeding program carried out by the inventor, William J. Colfer, in Chowchilla, Calif., in 2002. The female or seed parent is the *Cynara scolymus* cultivar designated 'GGMSC5' (unpatented). The male or pollen parent is the *Cynara scolyrmus* cultivar designated 'GGMSC5ER' (unpatented). The new *Cynara* cultivar was discovered and selected by the inventor, as a single flower plant within the progeny of the stated cross in a controlled environment in (2001) in Chowchilla, Calif.

Asexual reproduction of the new *Cynara* cultivar by vegetative cuttings was first performed in July of 2003 in Watsonville, Calif., and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'PS-MSG0417', which in combination distinguish this *Cynara* as a new and distinct cultivar:

1. numerous bud numbers;
2. fleshiness of bracts;
3. fleshiness of hearts;
4. uniformity of head shapes; and
5. high fecundity rate. (high fecundity rate (viable seed production) It should be noted that these data were collected from first year transplants.

Plants of the new *Cynara* cultivar 'PS-MSG0417' differ from plants of the parents, 'GGMSC5' (unpatented) and 'GGMSC5ER' (unpatented) in the following characteristics described in Table 1.

TABLE 1

| Character | New Cultivar 'PS-MSG0417' | Female Parent 'GGMSC5' (unpatented) | Male Parent 'GGMSC5ER' (unpatented) |
|---|---|---|---|
| Average Head Number | 6.86 | 5.45 | 4.32 |
| Head Shape | Oval | Oval | Oval |
| Head Color | Green | Green | Green |
| Average Plant Height (cm) | 116.84 | 121.92 | 132.08 |

Of the many commercial cultivars known to the present inventor, the most similar in comparison to the new *Cynara* cultivar 'PS-MSG0417' is the *Cynara* cultivar (Green Globe (unpatented), in the following characteristics described in Table 2:

TABLE 2

| Characteristic | New Cultivar 'PS-MSG0417' | Green Globe (unpatented) |
|---|---|---|
| Average Head Number | 6.86 | 5.2 |
| Fleshiness of bract (cm) | 0.53 | 0.49 |
| Uniformity of head shapes Rating Scale: (1-5) | 4.7 | 3.8 |
| Postproduction longevity | Good | Moderate to good |

BRIEF DESCRIPTION OF THE DRAWINGS

The accompanying photographs illustrate the overall appearance of the new *Cynara* cultivar 'PS-MSG0417' showing the colors as true as is reasonably possible with colored reproductions of this type. Colors in the photographs may differ slightly from the color values cited in the detailed botanical description, which accurately describe the color of 'PS-MSG0417'.

DETAILED BOTANICAL DESCRIPTION

Figure 1:
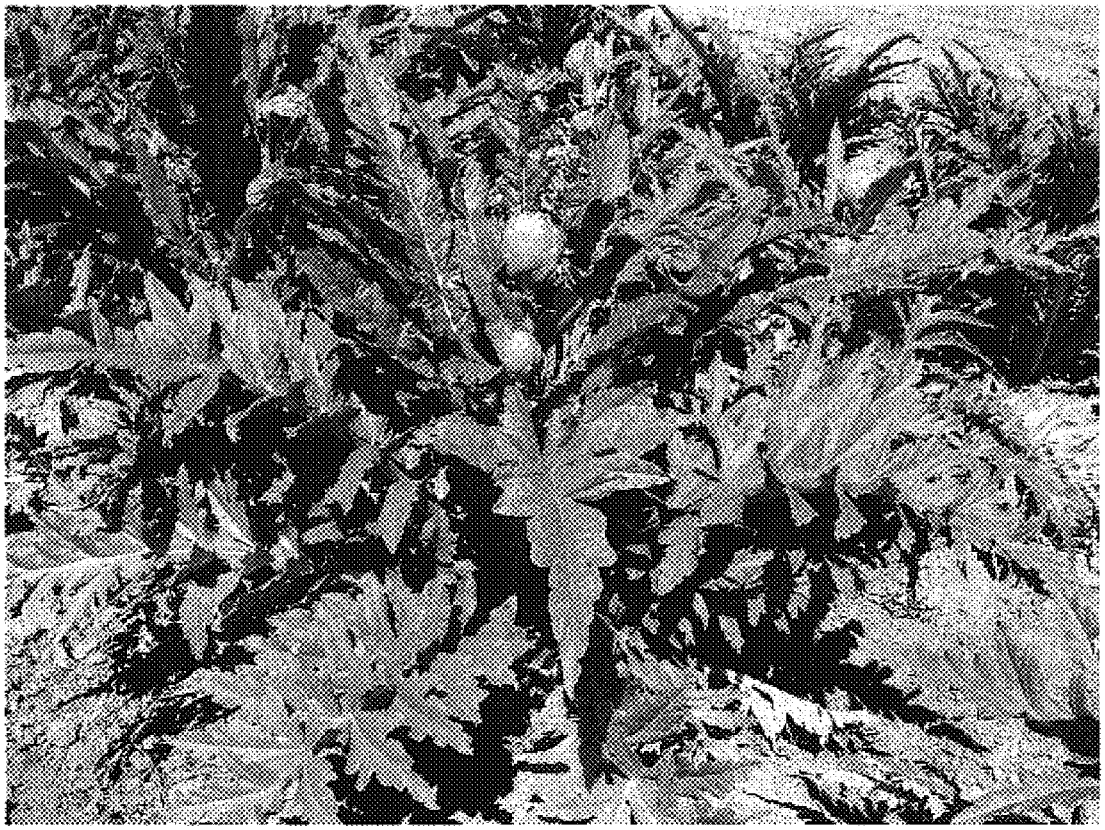
FIG. 1 shows an arial view of one complete 'PS-MSG0417' plant grown in the field.
Figure 2:
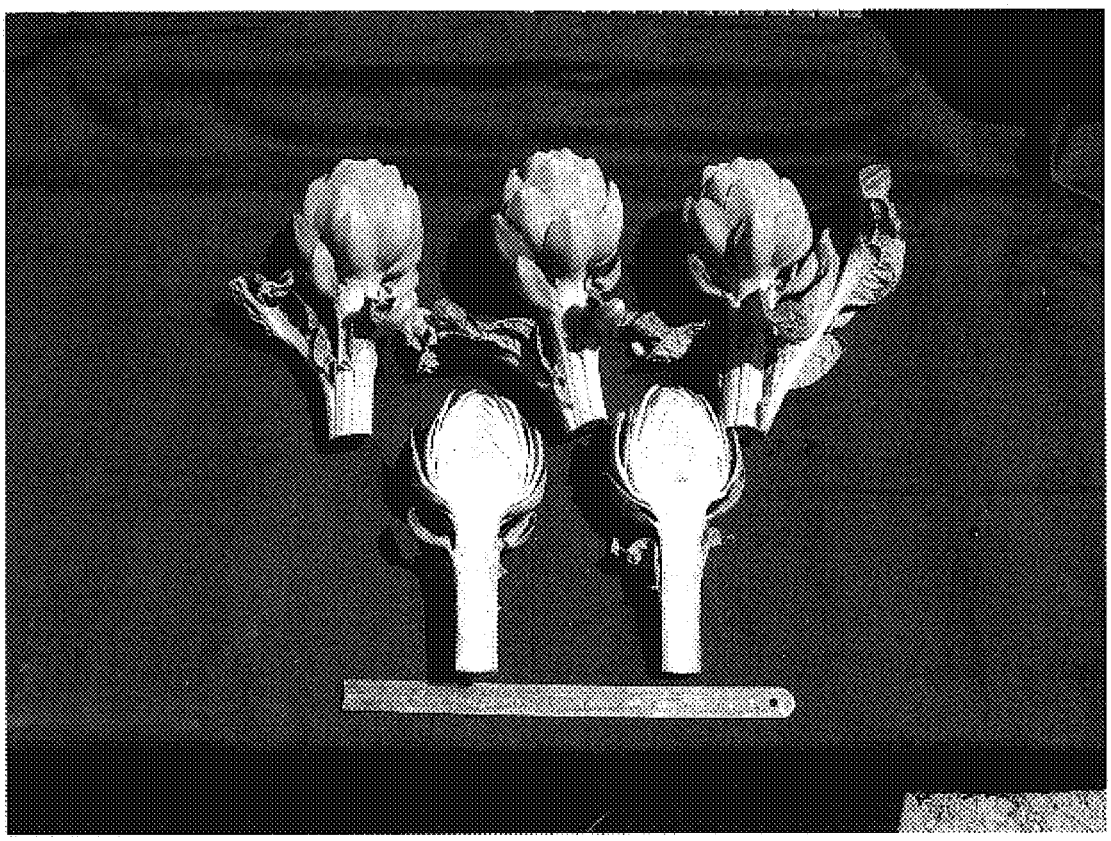
FIG. 2 shows a close-up of both the side view and vertical cross-section view of typical fruit, with their attached leaves, produced by 'PS-MSG0417'.

The new *Cynara* cultivar 'PS-MSG0417' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'PS-MSG0417' as grown in Castroville, Calif., under conditions which closely approximate those generally used in horticultural practice.

Castroville is located in California's central coast. Conditions can vary greatly during the summer months. Air temperature can range between the low 20's (degrees Fahrenheit) in the winter to above 80 (degrees Fahrenheit) during the summer months. Relative humidity is generally moderate with values ranging from the mid 40's to the high 60's. Prevailing winds are westerly, and rainfall rarely exceeds 25" (inches) of rainfall.

In the following description, holding quality was measured by the physical appearance of the harvested heads. This includes the heads appearance following 3, 7 and 10 day storage periods in a cold storage room held at 34 (degrees Fahrenheit). Head exterior (oxidation) was observed at each of the three observation points. Browning and blackening of plant tissue was evaluated as light, moderate and extreme. Juiciness was measured by observing exudate and rated as absent, moderate or excessive. Overall storage response was measured by observations concentrated on visible color variability and/or presence of lesions or other cosmetic anomalies. Leaf ratio (L/W) was determined by dividing representative leaf sample length measurements by representative leaf sample width measurements. Finally, head response to (weather) was determined by observing the heads at maturity. These field observations focus on presence or absence of bronzing, necrotic and chlorotic lesions or any abiotic response to environmental conditions. These data are reported as the possible causal event(s), and then describe the detailed head and plant responses.

The age of the plants in the aforementioned photographs, together with the following observations, measurements and values describe plants of 'PS-MSG0417' about 270 to 285 days from transplanting. Plants were developed in transplant trays for about 120 to 130 days, for a total plant age of about 390 to 415 days. Not all greenhouse plantings are performed on the same day. Physical data collection may also be performed on different days.

All color references below are measured against The Munsell Book of Color, Munsell Color Macbeth Division of Kollmorgen Instruments Corporation, (1988/PRO88-A). Colors are approximate as color depends on horticultural practices such as light level and fertilization rate, among others.

Classification:
- *Botanical.*—*Cynara scolymus L.*
- *Commercial.*—Artichoke c.v. 'PS-MSG0417.'

Parentage:
- *Female or seed parent.*—*Cynara scolymus* cultivar designated 'GGMSC5' (unpatented).
- *Male or pollen parent.*—*Cynara scolymus* cultivar designated 'GGMSC5ER' (unpatented).

Propagation: Vegetative cuttings.

Plant:
- *Height.*—About 116.84 cm. Range: 106.68 cm to 127.00 cm.
- *Width.*—About 179.20 cm. Range: 170.10 cm to 182.00 cm.
- *Growth habit.*—Upright/intermediate.
- *Vigor.*—Good. (This measurement is based on overall plant performance. Including plant height, density of leaf canopy and overall plant growth and development rates).

Large shoots: These offshoots or suckers from axillary buds are borne at the base of the stem sust below the soil surface.
- *Number per plant.*—About 5 or 6.
- *Length.*—About 19.72 cm. Range: 18 cm to 22 cm.
- *Diameter.*—About 2.04 cm. Range: 1.7 to 2.4 cm.
- *Color.*—Munsell Color: Wide range of colors: 5GY 7/6-5GY 6/6-5GY 5/6-5GY 4/4. Anthocyanin coloration range: 2.5R 5/4 - 2.5R 4/4 - 2.5R ¾.
- *Foliage density.*—Open to moderate, variable shoots give plant a open to moderate plant density appearance.
- *Side shoot development.*—Moderate side shoot development.
- *Number of leaves per side shoot.*—Ranges from 4 to 8.

Stem (main):
- *Length.*—About 26.53 cm. Range: 21.6 cm to 30.2 cm.
- *Diameter.*—About 6.43 cm. Range: 5.6 cm to 7.4 cm.
- *Width (with leaves).*—Ranges from 7.40 cm to 9.50 cm.
- *Color.*—Color Designation: 5GY 4/4-5GY 5/4-5GY 6/6 green coloration with basal anthocyanin coloration: 5R 5/4-5R 4/4.
- *Texture.*—Stem texture can vary from areas that are tomentum to tomentose. Maturity and prescence of surrounding leaf tissue influence stem pubescence.
- *Number of leaves per main stem.*—Ranges from 12 to 20.
- *Distance between leaf lobes (use petiole or leaf insertion not lobes) on stem.*—Ranges from 6.0 cm to 10.1 cm.

*Internode length.*—Ranges from 8.8 cm to 12.2 cm (Internode length influenced by soil conditions (moisture) in the field.

Bud:

*Shape.*—Typically ovate. Range from slightly round to oval.

*Height.*—Ranges 10.65 cm to 11.68 cm.

*Diameter.*—Ranges 10.41 cm to 10.97 cm.

*Color.*—Color dependent on bud age and exposure angles to the sun. Ranges 5 GY 5/6 - 5 GY 6/6 -2.5 GY 5/8.

*Texture.*—Glabrous, with some light pubescence at the base of the buds.

Inflorescence: Mature, meaning grown to point of harvest and ready for consumption.

*Florets.*—Number per primary head: Range of about 870 to 1287. Overall Shape: Tubulose, fused basal region flares to a flattened, expanded obtuse apex. Width: About 0.5 mm. Color: Color dependent on floret age. Ranges 10 PB 7/4 - 10 PB 7/6 -10 PB 7/8. Petals oxidize to tan colors late in maturation. Margin: Primarily entire. Texture: Smooth.

Capitulum (head):

*Number.*—About 6.86/plant. Range: 6.0 to 8.0 heads/plant.

*Shape.*—Oval. Oval shape can have increased mid-section dimensions.

*Size.*—(12) Primary: 36.20 cm to 38.10 cm. (18) Secondary: 28.58 cm to 30.40 cm. (30) Tertiary: 28.58 cm to 30.48 cm. (36) Tertiary: 26.04 cm to 27.94 cm. (48) Tertiary: 23.50 cm to 25.40 cm.

*Texture.*—The outer bracts are predominately smooth with very subtle narrow bands or grooves running the length of the bracts. These striac are not uniform on the bract surfaces.

*Color.*—Color Designation: 5 GY 5/6 - 5GY 6/4 - 5GY 6/6.

*Fragrance.*—Mild, lightly aromatic. Slightly sweet aroma.

*Firmness.*—Heads are moderately firm. Some head types in the spring have reduced firmness.

*Gloss.*—Dull. Heads have very little glossiness.

*Juiciness.*—Absent. Peduncle and bract exudate is slight.

Peduncle:

*Length.*—Ranges 7.62 cm to 8.38 cm.

*Diameter.*—Ranges 3.81 cm to 4.11 cm.

*Color.*—Color Designation: 5GY 4/4-5GY 5/4-5GY 6/6. Pubescence density influence the color range.

*Texture.*—Early development can be tomentose while later development can be delicately tomentos. Distinct bands or grooves are also evident; running the length of the peduncle.

Bract:

*Number.*—About 80.50 bracts. Range: 76 to 86 bracts.

*Arrangement.*—The bracts layer and overlap attaching to a fleshy receptacle.

*Length.*—Inner: Ranges from 6.67 cm to 7.87 cm. Outer: Ranges from 7.67 cm to 8.17 cm.

*Width.*—Inner: Ranges from 4.15 cm to 4.67 cm. Outer: Ranges from 4.95 cm to 5.85 cm.

*Shape.*—Bracts are predominantly oval shaped with constricted (narrow) basal regions on outer bracts and inner bracts are slightly rounded at the base.

*Texture.*—Smooth, slight texture.

*Color (inner).*—Bract Interior: 5 GY 4/6 - 5 GY 6/6 (Green). Outer bract interior, apex: 2.5 GY 8/6 - 7.5 Y 9/6 (Green-Yellow). More interior bracts on the basal portions of the bracts.

*Color (outer).*—Exterior coloration of bract 5 Y 8.5/6 - 7.5 Y 8.5/6 (Green) 5GY4/4-5GY5/6-7.5Y 8/8-10Y8.5/8 (Green coloration with basal yellow coloration).

*Firmness.*—Moderate. Bracts are brittle with reduced malleability. Outer bracts arc more flexible.

*Spinosity.*—Present or none. Spines are present. Length ranges between 1 mm to 3 mm in length.

*Basal thickness.*—About 5.33 mm. Range: 4.67 mm to 6.0 mm.

Heart:

*Description.*—Concave, full. Heart is slightly concave with broad outer margins.

*Color.*—5 Y 9/2 - 7.5 Y 9/2.

Pappus:

*Number.*—The pappus attaches at the apical region of the mature seed. Approximately 43–54 pappus filaments per seed. Seed numbers vary - about 870 to 1 287 seeds per head. The seed number vary greatly; dependent upon weather conditions, pollination, fertilization and seed-set which consequently influences pappus numbers.

*Length.*—About 17.30 mm. Range: 15.0 mm to 19.0 mm.

*Color.*—Variable white coloration.

Overall cold storage response: Good cold storage response. Slight oxidation observed (light browning).

Cold storage (hold quality): Good. Only a slight "browning" was observed on some bract edges.

Head exterior (oxidation): Moderate. Only those areas damaged during harvest showed some oxidation.

Head response (weather): None. No adverse plant responses were observed.

Foliage:

Leaf:

*Shape.*—Irregular, dentate leaves that arc long and strap-like, parted pinnatisect margins, and a slightly reduced tomentose upper leaf surface and more advanced tomentose lower leaf surface. The leaf apex is described as a reduced mucronulate.

*Length.*—About 113.92 cm. Range: 109.6 cm to 118.5 cm.

*Width.*—About 54.69 cm. Range: 52.27 cm to 57.03 cm.

*Leaf ratio (L/W).*—About 2.07. Range: 1.91 to 2.16.

*Leaf area.*—About 6,206.68 $cm^2$. Range: 5,995.37 $cm^2$ to 6,440.00 $cm^2$.

*Leaf serrations. About* 29.57 mm. Range: 13.0 mm to 46.0 mm.

*Leaf distance between serrations.*—About 49.7 mm. Range: 38.0 mm to 75.0 mm.

*Leaf basal angle.*—About 47.40 degrees. Range: 38.0 degrees to 62.0 degrees.

*Leaf basal thickness.*—About 14.83 mm. Range: 14.33 mm to 15.33 mm.

*Leaf area.*—About 6,206.68 $cm^2$. Range: 5,995.37 $cm^2$-to 6,440.00 $cm^2$.

*Texture.*—The mature leaves upper surface is lightly verrucose while the lower surface is nearly glabrous and smooth. Immature leaves especially near the mid-vein tend to be more verrucose on the upper surface and tend to be more tomentum on the lower leaf surfaces.

*Pubescence.*—Smooth to sparse density. Pubescence on most leaves is indistinct. Immature, younger leaves are highly pubescent on both surfaces but become reduced on the upper leaf surface as the leaf matures. Lower leaf surface is more pubescent throughout the leaf's development.

*Color.*—5 GY 4/4 - 5 GY 6/6 (upper leaf surface) 5 GY 6/2 (younger lower leaf surface) to 5 GY 6/4 (slightly older leaf surface).

Lobes:

*Number per leaf.*—About 6 to 10 (This number can also vary and is influenced by soil types and winter growth conditions).

*Apex shape.*—Apex can vary obtuse to acute depending on leaf maturity and developmental stages in relation to reproductive bolting.

*Base shape.*—Generally described as pinnatisect and lobed.

*Length.*—Ranges 1.2 cm to 4.6 cm. (Dependent upon leaf developmental stages).

*Width.*—Ranges 1.27 cm to 3.30 cm.

Venation: Prominent, greenish/white. Both mid-vein and surrounding venation are light green colored.

*Pattern.*—Light green/whitish mid-vein with green venation radiating from leaf mid-vein. Venation pattern is described as pinnate.

*Color.*—Greenish/white: Light transparent green coloration near 5GY 8/4.

Petiole:

*Length.*—About 22.89 cm. Range: 16.2 cm to 27.6 cm.

*Width.*—About 4.14 cm. Range: 3.7 cm to 4.7 cm.

*Diameter.*—About 1.43 cm. Range: 1.2 cm to 1.7 cm.

*Color.*—Color Designation: Color designation very similar to stem coloration: 5GY 4/4 - 5GY 5/4 - 5GY 6/6. Anthocyanin coloration: 5R 5/4 - 5R 4/4.

Reproductive organs/seeds: Seed are generally a light tan color with variable black specks on the seed coat. Seed has an oval (acute basal apex) shape. About 4 to 5 mm (w)×9mm (l).

Weather tolerance: No testing has been conducted or PS-MSG0417 is sensitive to temperatures below 20° F.

Disease/pest resistance: No observations made.

Disease/pest susceptibility: No observations made.

General observations: This new artichoke cultivar is a unique type that exhibits the following characteristics. The plants moderate height, ranging from 106 cm to 127 cm. Its comparative head qualities to California's artichoke variety 'Green Globe' include: green (non-glossy) exterior coloration, greater head numbers. Head numbers ranging from 6 to 8 heads per plant. Head shape does have slight variation displaying a predominately oval shapes and, slightly broadened mid-sections, oval shapes. These non-glossy heads are produced in the sizes ranging from (12) primary, size (18) secondaries and size (30, 36 and 48) tertiaries. Floral stalk development and head numbers can vary. Anthocyanin coloration is not present in innermost interior bracts. The head spinosity is present on bract apexes. Inner bracts also display spines but can be very slightly notched. The average spine length ranges between 1.8–3.0 mm. The plants upright growth habit is intermediate, but is very vigorous. The canopies coloration is a deeper green/green/yellow color with some colors ranging towards darker green/green hues. These colors on Munsell Leaf Color Chart range from 5 GY 4/4–5 GY 6/6. Leaf spinosity is light to moderate, categorized as few. Floral stalk development during anthesis produces a purple flower. Flower color varies with flower maturity. The phenotypic characteristics of this cultivar may vary slightly, depending upon variation in the environmental factors. Including weather (temperature, humidity and light intensity), day length, soil type, farming practices, location and time of year.

I claim:

1. A new and distinct cultivar of artichoke plant named 'PS-MSG0417', as described and illustrated.

* * * * *

UNITED STATES PATENT AND TRADEMARK OFFICE

CERTIFICATE OF CORRECTION

PATENT NO. : PP 20,232 P3
APPLICATION NO. : 11/416318
DATED : August 25, 2009
INVENTOR(S) : Colfer It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (420) days Delete the phrase "by 420 days" and insert -- by 534 days --

Signed and Sealed this

Twenty-fifth Day of May, 2010

David J. Kappos

David J. Kappos
*Director of the United States Patent and Trademark Office*